United States Patent [19]

Ishikawa et al.

[11] Patent Number: 4,558,148
[45] Date of Patent: Dec. 10, 1985

[54] FLUORINATED ALLYLIC COMPOUNDS AND A PROCESS FOR PREPARING THESE COMPOUNDS

[75] Inventors: Nobuo Ishikawa, Yokohama; Tomoya Kitazume, Tokyo, both of Japan

[73] Assignee: Daikin Industries Ltd., Osaka, Japan

[21] Appl. No.: 635,682

[22] Filed: Jul. 30, 1984

[30] Foreign Application Priority Data

Jul. 30, 1983 [JP] Japan ................................. 58-140116
Jul. 30, 1983 [JP] Japan ................................. 58-140117

[51] Int. Cl.$^4$ ........................... C07F 7/18; C07F 7/08; C07C 33/46; C07C 33/42
[52] U.S. Cl. .................................. 556/488; 568/812; 568/843; 548/460; 549/4; 549/78; 549/427; 549/505
[58] Field of Search ................ 568/812, 843; 556/488; 549/4, 78, 427, 505; 548/460

[56] References Cited

U.S. PATENT DOCUMENTS 2,490,753 12/1949 Hill et al. ......................... 568/843 X
3,576,888 4/1971 Lichstein et al. ................. 568/843

FOREIGN PATENT DOCUMENTS 59-46235 3/1984 Japan .................................. 568/843
1601345 10/1981 United Kingdom ................ 568/843

Primary Examiner—Paul F. Shaver
Attorney, Agent, or Firm—Armstrong, Nikaido, Marmelstein & Kubovcik

[57] ABSTRACT

There are described fluorinated allylic compounds as expressed by the following general formula

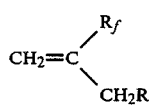

wherein $R_f$ is a fluorinated aliphatic group and R is a group expressed by a general formula

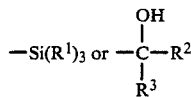

wherein $R^1$ is an aliphatic or aromatic hydrocarbon group and $R^2$ and $R^3$ are the same group or different groups as selected among hydrogen atom, aliphatic and aromatic hydrocarbon groups, and heterocyclic groups. Further, a process of preparing fluorinated allylic compounds is described which includes a process step wherein a silane metal halide as expressed by a general formula

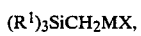

wherein $R^1$ is either an aliphatic or aromatic hydrocarbon group, M is an element that belongs to the group IIa, IIIb, or VIIb of the periodic table, and X is a halogen atom, is reacted with a fluorinated carboxylic acid ester as expressed by a general formula

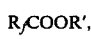

wherein $R_f$ is a fluorinated aliphatic group and R' is either an aliphatic or aromatic hydrocarbon group, to form a fluorinated carbinol as expressed by a general formula

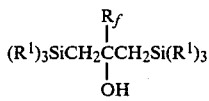

wherein $R^1$ and $R_f$ are as defined above, and further a molecule of $(R^1)_3SiOH$, where $R^1$ is as defined above, is eliminated from this carbinol to produce a fluorinated allylsilane as expressed by a general formula

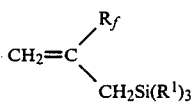

wherein $R^1$ and $R_f$ are as defined above.

13 Claims, No Drawings

FLUORINATED ALLYLIC COMPOUNDS AND A PROCESS FOR PREPARING THESE COMPOUNDS

BACKGROUND OF THE INVENTION

1. Field of the Invention

This invention relates to fluorinated allylic compounds and a process of their preparation.

2. Description of the Prior Art

In recent years, fluorinated compounds have attracted much attention in various fields for their applications as medicines, agricultural chemicals, various surface treatment agents, etc. It is important to provide a method to introduce fluorine on a selected position of a molecule easily and with high yield, but only very few methods are reported, for example, α-trifluoromethyl malonic acid ester publicated at the 8th Fluorine Chemistry Symposium, Japan (1982). The invention was made to provide one of the method to solve the above problem.

OBJECTS AND SUMMARY OF THE INVENTION

Accordingly, it is an object of the present invention to provide fluorinated allylic compounds having a fluorinated group, for example $CF_3$, at an desired position of their molecule and applicable to introduce such fluorinated group in the molecule of another compound.

More specifically, the invention is intended to provide fluorinated allylic compounds of the general formula

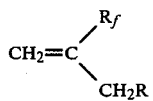

wherein $R_f$ is a fluorinated aliphatic group and R is a group of the general formula

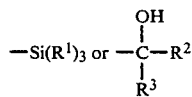

wherein $R^1$ is an aliphatic or aromatic hydrocarbon group and $R^2$ and $R^3$ are either the same group or different group as selected from the group consisting of hydrogen atom, aliphatic and aromatic hydrocarbon groups, and heterocyclic groups.

These fluorinated allylic compounds are known to be useful as the weed killer, insecticide, and other physiologically active substances, intermediates of the building block of these physiologically active substances, or as the fluorinated alcoholic solvent.

It is another object of the invention to provide a process for preparing these fluorinated allylic compounds readily at high yield that includes a step wherein a silane metal halide of the general formula

wherein $R^1$ is either an aliphatic or aromatic hydrocarbon group, M is an element that belongs to the group IIa, IIIb, or VIIb of the periodic table, and X is a halogen atom, is reacted with a fluorinated carboxylic acid ester of the general formula

wherein $R_f$ is a fluorinated aliphatic group and R' is either an aliphatic or aromatic hydrocarbon group, to form a fluorinated carbinol of the general formula

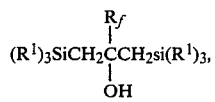

wherein $R^1$ and $R_f$ are as defined above, and further a molecule of $(R^1)_3SiOH$ is eliminated from this carbinol to produce a fluorinated allylsilane of the general formula

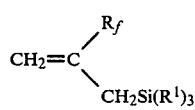

wherein $R^1$ and $R_f$ are as defined above.

The above fluorinated allylsilane compound can be further reacted with a carbonyl compound of the general formula

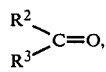

wherein $R^2$ and $R^3$ are the same or different groups selected from the group consisting of hydrogen atom, aliphatic and aromatic hydrocarbon groups, and heterocyclic groups and these groups may be substituted, to derive a fluorinated hydroxybutene of the general formula

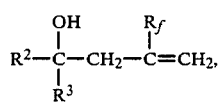

wherein $R^2$, $R^3$ and $R_f$ are as defined above.

Other objects and advantages of the invention will become apparent from the following description of embodiments.

DESCRIPTION OF THE PREFERRED EMBODIMENTS

In the above general formula representing the fluorinated allylic compounds embodying the invention, for the $R_f$, a fluorinated aliphatic group as expressed by a general formula $CF_3(CF_2)_m$— or $(CF_3)_2CF(CF_2)_n$—in which m is an integer of 0 to 9 and n is an integer of 0 to 6. Examples of such group are $CF_3$—, $CF_3CF_2$—, $CF_3(CF_2)_2$—, $CF_3(CF_2)_3$—, $CF_3(CF_2)_4$—, $CF_3(CF_2)_5$—, $(CF_3)_2CF$—, $(CF_3)_2CFCF_2$—, $(CF_3)_2CF(CF_2)_2$—, $(CF_3)_2CF(CF_2)_3$—, etc. Beside the above fluorinated alkyl groups, unsaturated fluorinated groups and particularly fluorinated alkenyl groups, for example, $CF_2=CF-CF_2$—, $CF_3-CF=CF$—, etc. are also applicable. In view of the solubility in solvent, however, the fluorinated aliphatic group used preferably has 10 or less carbon atoms. In addition to the perfluoroalkyl and perfluoroalkenyl groups as mentioned above, it is also possible to use partially fluorinated alkyl or alkenyl groups with a hydrogen atom or atoms partially left in their molecular chain, for example, $CF_3(CF_2)_2CH_2CF_2-$. Further, $R_f$ may be a fluorinated aliphatic group with an aromatic substituent, for example, $C_6H_5-CF_2-$, $C_6H_5-(CF_2)_2-$, etc.

On the other hand, $R^1$, $R^2$, and $R^3$ in the same general formula may be selected among alkyl groups, for example, methyl, ethyl, propyl, isopropyl, butyl, and isobutyl groups, and partially unsaturated alkenyl groups though they preferably have 10 or less carbon atoms. Beside the above, aryl groups and aralkyl groups, for example, those with a substituent or substituents selected among the alkyl groups as mentioned above may be used for $R^1$ while aryl groups and aromatic heterocyclic groups, for example, furan, thiophene, pyrrole and pyran groups may be used for $R^2$ and $R^3$.

On the other hand, in the silane metal halide $(R^1)_3SiCH_2MX$, which is used in the aforementioned process step of preparing the fluorinated allyl compound in accordance to the present invention, $R^1$ is selected as mentioned above, M is an element that belongs to the group IIa of the periodic table representing magnesium and other alkaline earth metals, group IIIb that includes cerium, yttrium, ytterbium, etc. or group VIIb that includes manganese, etc., and X is a chlorine or bromine atom. In the fluorinated carboxylic acid ester $R_fCOOR'$ used in the same process step, $R_f$ may be selected among various fluorinated aliphatic groups that are already cited for such while R' may be among the same aliphatic and aromatic hydrocarbon groups as cited for $R^1$.

$(R^1)_3SiOH$ as mentioned above can be eliminated from the fluorinated carbinol

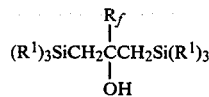

by the action of acid or alkali. Examples of applicable acid are sulfuric acid, phosphoric acid, and trifluoroacetic acid while an example of applicable alkali is KH.

Further, in the general formula of the carbonyl compound provided in the form of aldehyde or ketone and used in the aforementioned process step of preparing the fluorinated hydroxybutene of the invention, $R^2$ and $R^3$ may be selected among groups as already cited for the groups $R^2$ and $R^3$ of fluorinated allylic compounds of the invention.

The invention will be described below with reference to an embodiment thereof wherein a $CF_3$ group is introduced in the allylsilane skeleton in accordance with a reaction formula as given next.

First, ethyl trifuloroacetate that is a cheap $CF_3$ source is reacted with a Grignard reagent 1 available from chloromethyltrimethylsilane and magnesium to give a carbinol 2. This carbinol is converted by the Peterson elimination reaction to β-trifluoromethylallylsilane 3 at good yield, for example, of 60%. This reaction can be expressed by the following formula in which a group $(CH_3)_3Si-$ group is abbreviated TMS:

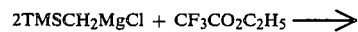

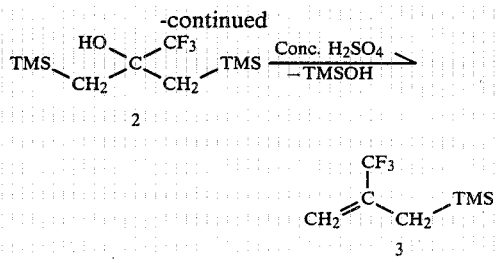

It is noted that in the above reaction TMSOH is eliminated by the action of conc. $H_2SO_4$ preferably at elevated temperature, for example, 50° to 60° C. and under reduced pressure, for example, 20 mmHg. Without such heating and reduced pressure, the other TMS group which is necessary for the product 3 is also often eliminated. The fluorinated allysilane 3 prepared by the above reaction has a boiling point of 106.5° to 107.0° C. At room temperature and under atmospheric pressure, it is stable enough to storage for a long time. It can be readily purified by distillation.

The allysilane 3 obtained by the above reaction was tentatively reacted with aldehyde $R^1CH=O$ that is one of the representative electrophilic reagents.

First, a process of prior art in which, as generally known, an unflorinated allylsilane and aldehyde are reacted in solvent methylene chloride using a Lewis acid, for example, $TiCl_4$, $BF_3.O(C_2H_5)_2$, or $ZnBr_2$ was tested. Namely, this process was applied as it was to react the fluorinated allylsilane 3 and aldehyde 4 in the following reaction but no target adduct product 5 was available.

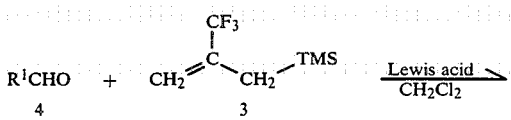

(no target product)

The authors thus used a tetraalkylammonium fluoride, for example, tetrabutylammonium fluoride (hereinafter abbreviated "TBAF") instead of the Lewis acid. They thus discovered that the target product, namely, adduct 5 was produced at high yield according to the following formula:

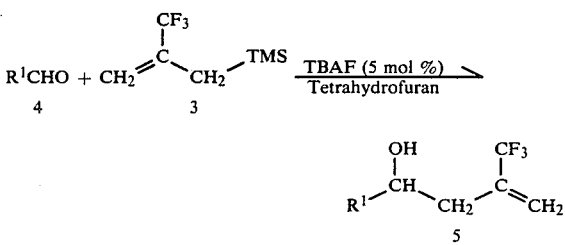

The above reaction completes in several hours at room temperature and under atmospheric pressure. Beside tetrahydrofuran, for example, dimethylformamide, dimethylsulfoxide, dimethylacetamide, N-methylpyrrolidone, hexamethylphosphamide, acetonitrile, etc. may be used for the solvent of the above reaction. Being characterized by high solvation energies with cations, these polar solvents are powerful solvents and therefore facilitate the reaction rate of anionic reagents therein.

The above two reactions could be well understood by assuming the following reaction mechanisms, respectively:

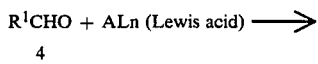

$$(R^1CH=O^+:A^-Ln \rightleftarrows R^1C^+H—OA^-Ln) \quad 6$$

where A: Ti, B or Zn; and L: Cl, F, Br

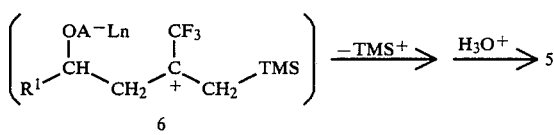

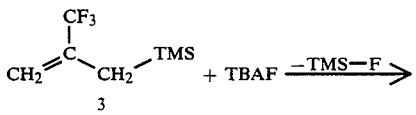

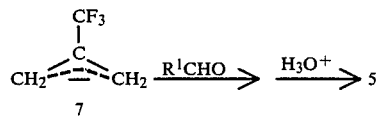

In the above two reaction mechanisms, formation of intermediates 6 and 7, respectively, is assumed. A difference between these intermediates in stability would then give a reason why when the Lewis acid is used the given reaction does not occur but with TBAF it proceeds successfully giving the target product 5 at high yield. Namely, the intermediate 6 is unstabilized under the strong electron attraction from the CF₃ group while the intermediate 7 is stabilized.

The present authors tested the above reaction variously making use of TBAF, which gave favorable results as summarized in the following table. These results proved that the allylsilane 3 as mentioned above is a useful compound and that the process step used gives a valuable method to prepare 4-substituted-2-trifluoromethyl-4-hydroxy-1-butenes with a trifluoromethyl group introduced at the target position (namely, β-position).

| | Reaction time, hr | Yield, % of product 5 |
| --- | --- | --- |
| Ph— | 2 | 85 |
| n-C₆H₁₃— | 2 | 82 |
| CH₃<br>\|<br>Ph—CH—CH₂— | 5 | 59 |
| (furyl) | 2 | 89 |
| CH₃\C=CH—CH₂—CH₂—CH(CH₃)—CH₂—<br>CH₃/ | 5 | 80 |
| CH₃\CH—CH₂—CH₂—<br>CH₃/ | 2 | 46 |

The present invention will be more clearly understood with reference to the following examples.

EXAMPLE 1

(1) Synthesis of a compound 2 by the following reaction:

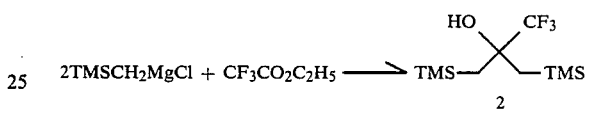

Magnesium (9.72 g, 0.4 mol) and diethyl ether (300 ml) were put into a three-necked flask (500 ml) and (CH₃SiCH₂Cl (49.1 g, 0.4 mol) was added dropwisely to synthesize (CH₃)₃SiCH₂MgCl. CF₃CO₂C₂H₅ (28.4 g, 0.2 mol) was then added dropwise for an hour into the solution of Grignard reagent thus prepared and the mixture was agitated for another hour. After, the reaction was quenched by 1N HCl and the oily layer was separated. Evaporation of the solvent followed by distillation under reduced pressure gave the product (37.9 g) in a yield of 70%. Boiling point was 85.0° to 86.0° C./14 mmHg.

The spectral data of the above product were as follows:

¹⁹F NMR (external standard:CF₃CO₂H): δ 4.0 (CF₃).
¹H NMR (solvent: CDCl₃): τ 9.96–9.88 (Si(CH₃)₃), 9.99–8.81 (CH₂×2), 8.50 (OH).
IR: 3600 cm⁻¹ (OH).
Elementary analysis: Found C (44.17), H (8.06). Calculated for C₁₀H₂₇OF₃Si₂: C (44.08), H (8.51).

(2) Synthesis of a compound 3 by the following reaction:

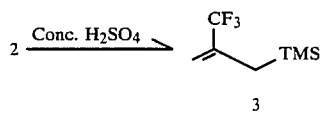

Into three-necked flask (25 ml) equipped with a dropping funnel and distillation column was added conc. H₂SO₄ (5ml). The compound 2 (1.53 g, 5.1 mol) was added dropwisely while the allylsilane 3, as it was formed, was distilled under reduced pressure to a trap. The product was redistilled to give the allysilane 3 (6.8 g) of boiling point 55° to 56° C./97 mmHg at a yield of 78%.

The spectral data of the above product were as follows:

¹⁹F NMR (external standard: CF₃CO₂H): δ −8.4 (CF₃).

¹H MNR (solvent: CDCl₃): τ 9.93 (Si(CH₃)₃), 9.39 (CH₂), 5.07, 4.55

( =<^H_H )

IR: 1650 cm⁻¹ (C=C).

EXAMPLE 2

Synthesis of a compound 5 by the following reaction:

PhCHO + =<^{CF_3}_{TMS} $\xrightarrow{\text{TBAF}}_{\text{Tetrahydrofuran}}$
4        3

$$\underset{5}{\text{PhCHCH}_2\text{—}\overset{\overset{\text{CF}_3}{|}}{\text{C}}\text{=CH}_2} \quad \overset{\overset{\text{OH}}{|}}{}$$

Benzaldehyde (0.24 g, 2.3 mmol), β-trifluoromethylallylsilane (0.36 g, 2.0 mmol) and tetrahydrofuran (5 ml) were put into a three-necked flask (25 ml). A solution of TBAF (0.1 ml, 0.1 mmol) in tetrahydrofuran was added dropwise to the above mixture. After a 2 hour reaction at room temperature, water was added and the oily substance formed was subjected to extraction with diethyl ether. After evaporation of solvent from the extracts, the residues were purified by column chromatography with use of a hexane-ether (10:1) solvent system. A yield of 85% was thus achieved.

The spectral data of the above product were as follows:

¹⁹F NMR (external standard: CF₃CO₂H): δ−10.2 (CF₃).

¹H NMR (solvent: CDCl₃): τ7.79 (OH), 7.50 (CH₂), 5.25 (CH), 4.68, 4.30

( =<^H_H )

2.75 (Ar-H).
IR: 3380 cm⁻¹ (OH).

EXAMPLE 3

Synthesis of a compound 5 by the following reaction:

C₆H₁₃—CHO + =<^{CF_3}_{TMS} $\xrightarrow{\text{TBAF}}_{\text{Tetrahydrofuran}}$
4              3

$$\underset{5}{\text{C}_6\text{H}_{13}\text{CHCH}_2\text{—}\overset{\overset{\text{CF}_3}{|}}{\text{C}}\text{=CH}_2} \quad \overset{\overset{\text{OH}}{|}}{}$$

Heptanal (0.24 g, 2.1 mmol), β-trifluoromethylallylsilane (0.36 g, 2.0 mmol) and tetrahydrofuran (5 ml) were put into a three-necked flask (10 ml) and a solution of TBAF (0.1 ml, 0.1 mmol) in tetrahydrofuran was added dropwise to the above mixture. After a 2 hour reaction at room temperature, water was added at the oily substance formed was subjected to extraction with diethyl ether. After evaporation of solvent, the residues were purified by column chromatography using a hexane-ether (10:1) solvent system. A yield of 82% was thus achieved.

The spectral data of the above product were as follows:

¹⁹F NMR (external standard: CF₃CO₂H): δ−10.0 (CF₃).

¹H NMR (solvent: CDCl₃): τ9.11 (CH₃), 9.37–9.89 (CH₂×5, OH), 7.77 (CH₂), 6.28 (C̲H̲OH), 4.24, 4.53

( =<^H_H )

IR: 3320 cm⁻¹ (OH).

EXAMPLE 4

Synthesis of a compound 5 by the following reaction:

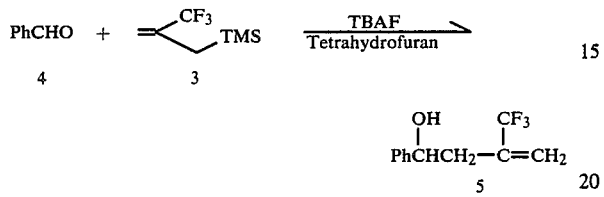

Citronellal (0.32 g, 2.1 mmol), β-trifluoromethylallylsilane (0.36 g, 2.0 mmol), and tetrahydrofuran (5 ml) were put into a three-necked flask (10 ml) and a solution of TBAF (0.1 ml, 0.1 mmol) was added dropwise to the mixture. After a 5 hour reaction at room temperature, water was added and the oily substance formed was subjected to extraction with diethyl ether. After evaporation of solvent, residues were purified by column chromatography using a hexane-ether (7:1) solvent system. A yield of 80% was thus attained.

The spectral data of the above product were as follows:

¹⁹F NMR (external standard: CF₃CO₂H): δ−9.95 (CF₃).

¹H NMR (solvent: CDCl₃): τ9.06 (CH₃), 8.35 (CH₃×2), 7.62–9.05 (CH₂×3, OH), 6.19 (C̲H̲OH), 4.97

( =<^H ), 4.25–4.55

( =<^H_H )

IR: 3375 cm⁻¹ (OH).

EXAMPLE 5

Synthesis of a compound 5 by the following reaction:

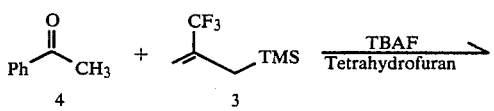
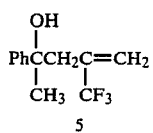

Acetophenone (0.26 g, 2.2 mmol), β-trifluoromethylallylsilane (0.36 g, 2.0 mmol), and tetrahydrofuran (5 ml) were put into a three-necked flask (25 ml) and a solution of TBAF (0.1 ml, 0.1 mmol) in tetrahydrofuran was added dropwise to the mixture. After a 2 hour reaction at room temperature, water was added and the oily substance formed was subjected to extraction with diethyl ether. After evaporation of solvent, the residues were purified by column chromatography using a hexane-ether (3:1) solvent system. A yield of 56% was thus achieved.

The spectral data of the above product were as follows:

$^{19}F$ NMR (external standard: $CF_3CO_2H$): δ−10.18 ($CF_3$).

$^{1}H$ NMR (solvent: $CDCl_3$): τ8.47 ($CH_3$), 8.23 (OH), 7.39 ($CH_2$), 4.72, 4.32

2.55–2.92 (AR—H).

IR: 3450 cm$^{-1}$ (OH).

What is claimed is:

1. Fluorinated allylic compounds of the general formula

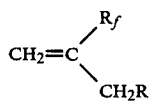

wherein $R_f$ is a fluorinated aliphatic group, and R is a group of the general formula

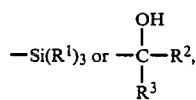

wherein $R^1$ is an aliphatic or aromatic hydrocarbon group and $R^2$ and $R^3$ are the same or different groups selected from the group consisting of hydrogen atom, aliphatic and aromatic hydrocarbon groups, and heterocyclic groups.

2. Fluorinated allylic compounds as claimed in claim 1 wherein $R_f$ is either a fluorinated alkyl or alkenyl group having 10 or less carbon atoms.

3. Fluorinated allylic compounds as claimed in claim 1 wherein $R^1$ is an alkyl, alkenyl, aryl or aralkyl group having 10 or less carbon atoms.

4. Fluorinated allylic compounds as claimed in claim 1 wherein $R^2$ and $R^3$ are selected from the group consisting of an alkyl, alkenyl, aryl, and oxygen, sulfur or nitrogen containing aromatic heterocyclic group having 10 or less carbon atoms.

5. A process for preparing a fluorinated allylic compound (1) of the general formula

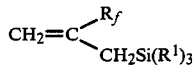 (1)

wherein $R_f$ is a fluorinated aliphatic group, and $R^1$ is an aliphatic or aromatic hydrocarbon group which comprises:

(a) reacting a silane metal halide of the formula $(R^1)_3SiCH_2MX$ wherein $R^1$ is the same as defined above, M is selected from the group consisting of the elements of IIa, IIIb and VIIb of the periodic table, and X is a halogen atom, with a fluorinated carboxylic acid ester of the formula

wherein $R_f$ is the same as defined above and R' is an aliphatic or aromatic hydrocarbon group, and (b) reacting the reaction mixture obtained above with an acid or alkali.

6. A process as claimed in claim 5 wherein said $R_f$ is a fluorinated alkyl or alkenyl group having 10 or less carbon atoms.

7. A process as claimed in claim 5 wherein said $R^1$ is an alkyl, alkenyl, aryl, or aralkyl group having 10 or less carbon atoms.

8. A process as claimed in claim 5 wherein said R' is an aliphatic or aromatic hydrocarbon group having 10 or less carbon atoms.

9. A process as claimed in claim 5 wherein said acid is sulfuric acid, phosphoric acid or trifluoroacetic acid.

10. A process as claimed in claim 5 wherein said alkali is potassium hydroxide.

11. A process for preparing a fluorinated allylic compound (2) of the general formula

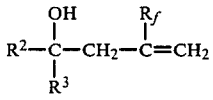 (2)

wherein $R^2$ and $R^3$ are the same or different and are selected from the group consisting of a hydrogen atom, an aliphatic or aromatic hydrocarbon group, and a heterocyclic group, and $R_f$ is the same as defined above, which comprises reacting the fluorinated allylic compound (1) with a carbonyl compound of the formula

wherein $R^2$ and $R^3$ are respectively the same as defined above in the presence of a tetraalkylammonium fluoride.

12. A process as claimed in claim 11 wherein said $R^2$ and $R^3$ are selected from the group consisting of an alkyl, alkenyl, aryl, and oxygen, sulfur or nitrogen containing aromatic heterocyclic group having 10 or less carbon atoms.

13. A process as claimed in claim 11 wherein said tetraalkylammonium is tetrabutylammonium.

* * * * *